United States Patent
Angelopoulos et al.

(10) Patent No.: US 11,132,920 B2
(45) Date of Patent: Sep. 28, 2021

(54) PERSONALIZED INTERVENTION BASED ON MACHINE LEARNING OF BEHAVIOR CHANGE STATES

(71) Applicant: International Business Machines Corporation, Armonk, NY (US)

(72) Inventors: Marie Angelopoulos, Cortlandt Manor, NY (US); Shahram Ebadollahi, White Plains, NY (US); Stewart T. Sill, Wake Forest, NC (US); Michal Rosen-Zvi, Jerusalem (IL); Ching-Hua Chen, New York, NY (US); James V. Codella, Danbury, CT (US); Si Sun, Whitestone, NY (US)

(73) Assignee: International Business Machines Corporation, Armonk, NY (US)

( * ) Notice: Subject to any disclaimer, the term of this patent is extended or adjusted under 35 U.S.C. 154(b) by 443 days.

(21) Appl. No.: 15/848,091

(22) Filed: Dec. 20, 2017

(65) Prior Publication Data
US 2019/0189025 A1    Jun. 20, 2019

(51) Int. Cl.
*G09B 19/00* (2006.01)
*H04L 12/58* (2006.01)
(Continued)

(52) U.S. Cl.
CPC ........ *G09B 19/0092* (2013.01); *A61B 5/0022* (2013.01); *G16H 20/00* (2018.01);
(Continued)

(58) Field of Classification Search
CPC .... G09B 19/00; G09B 19/02; G09B 19/0092; G16H 20/00; A61B 5/0022; H04L 51/046;
(Continued)

(56) References Cited

U.S. PATENT DOCUMENTS

| 5,207,580 A | 5/1993 | Strecher |
| 5,596,994 A | 1/1997 | Bro |

(Continued)

OTHER PUBLICATIONS

Nudelman et al., Mapping Health Behaviors: Constructing and Validating a Common-Sense Taxonomy of Health Behaviors, Social Science & Medicine, Elsevier, Oct. 9, 2015, 146, pp. 1-10.
(Continued)

*Primary Examiner* — Timothy A Musselman
(74) *Attorney, Agent, or Firm* — Will Stock; Edell, Shapiro & Finnan, LLC

(57) ABSTRACT

A system provides an intervention for a user and comprises at least one processor. The system monitors behavior and context of a user to generate a behavior history. One or more models are utilized to determine an intervention for the user to induce a behavior modification, wherein the one or more models map interventions to user context and behavior and utilize the behavior history to determine an effective intervention for the user. The intervention is provided to the user and feedback is received in response to the intervention. The one or more models are updated based on the feedback. Embodiments of the present invention further include a method and computer program product for providing an intervention to a user in substantially the same manner described above.

17 Claims, 6 Drawing Sheets

(51) Int. Cl.
*H04L 29/08* (2006.01)
*A61B 5/00* (2006.01)
*G16H 20/00* (2018.01)
*H04M 1/72403* (2021.01)
*H04M 1/72454* (2021.01)

(52) U.S. Cl.
CPC ............ *H04L 51/046* (2013.01); *H04L 67/12* (2013.01); *H04L 67/22* (2013.01); *H04M 1/72403* (2021.01); *H04M 1/72454* (2021.01)

(58) Field of Classification Search
CPC .............. H04L 51/12; H04M 1/72522; H04M 1/72569
See application file for complete search history.

(56) References Cited

U.S. PATENT DOCUMENTS

| | | | |
|---|---|---|---|
| 5,813,863 A | 9/1998 | Sloane et al. | |
| 5,908,301 A | 6/1999 | Lutz | |
| 5,967,789 A | 10/1999 | Segel et al. | |
| 6,039,688 A | 3/2000 | Douglas et al. | |
| 8,540,517 B2* | 9/2013 | Williams | G09B 19/00 |
| | | | 434/236 |
| 2001/0031451 A1 | 10/2001 | Sander et al. | |
| 2003/0027116 A1 | 2/2003 | O'Donnell | |
| 2003/0186202 A1 | 10/2003 | Isenberg | |
| 2004/0247748 A1 | 12/2004 | Bronkema | |
| 2007/0072156 A1 | 3/2007 | Kaufman et al. | |
| 2008/0126277 A1 | 5/2008 | Williams et al. | |
| 2011/0307228 A1* | 12/2011 | Kasabov | G06N 20/00 |
| | | | 703/2 |
| 2014/0099614 A1 | 4/2014 | Hu et al. | |
| 2014/0335490 A1 | 11/2014 | Baarman et al. | |
| 2015/0243176 A1* | 8/2015 | Zaslavsky | G06Q 50/20 |
| | | | 434/322 |

OTHER PUBLICATIONS

Michie et al., The Behaviour Change Wheel: A New Method for Characterising and Designing Behaviour Change Interventions, Implementation Science, Apr. 23, 2011, 6:42, pp. 1-12.

* cited by examiner

PERSONALIZED INTERVENTION BASED ON MACHINE LEARNING OF BEHAVIOR CHANGE STATES

BACKGROUND

1. Technical Field

Present invention embodiments relate to communication systems, and more specifically, to providing personalized interventions for individuals at appropriate times and frequencies of occurrence for helping them achieve their health and life goals, that is contextual based, dynamic, and based on machine learning.

2. Discussion of the Related Art

Helping people achieve their health and life goals is a complex process involving multiple, interacting factors, including personal goals, motivation, capability, and opportunity. Existing mechanisms (e.g., mobile telephone applications) produce digital interventions for users to enable behavior modification. However, these mechanisms are largely unsuccessful at inducing the desired behavior changes.

SUMMARY

According to one embodiment of the present invention, a system provides an intervention for a user and comprises at least one processor. The system monitors behavior and context of a user to generate a behavior history. One or more models are utilized to determine an intervention for the user to induce a behavior modification, wherein the one or more models map interventions to user context and behavior and utilize the behavior history to determine an effective intervention for the user. The intervention is provided to the user and feedback is received in response to the intervention. The one or more models are updated based on the feedback. Embodiments of the present invention further include a method and computer program product for providing an intervention to a user in substantially the same manner described above.

BRIEF DESCRIPTION OF THE DRAWINGS

Generally, like reference numerals in the various figures are utilized to designate like components.

DETAILED DESCRIPTION

Figure 1:
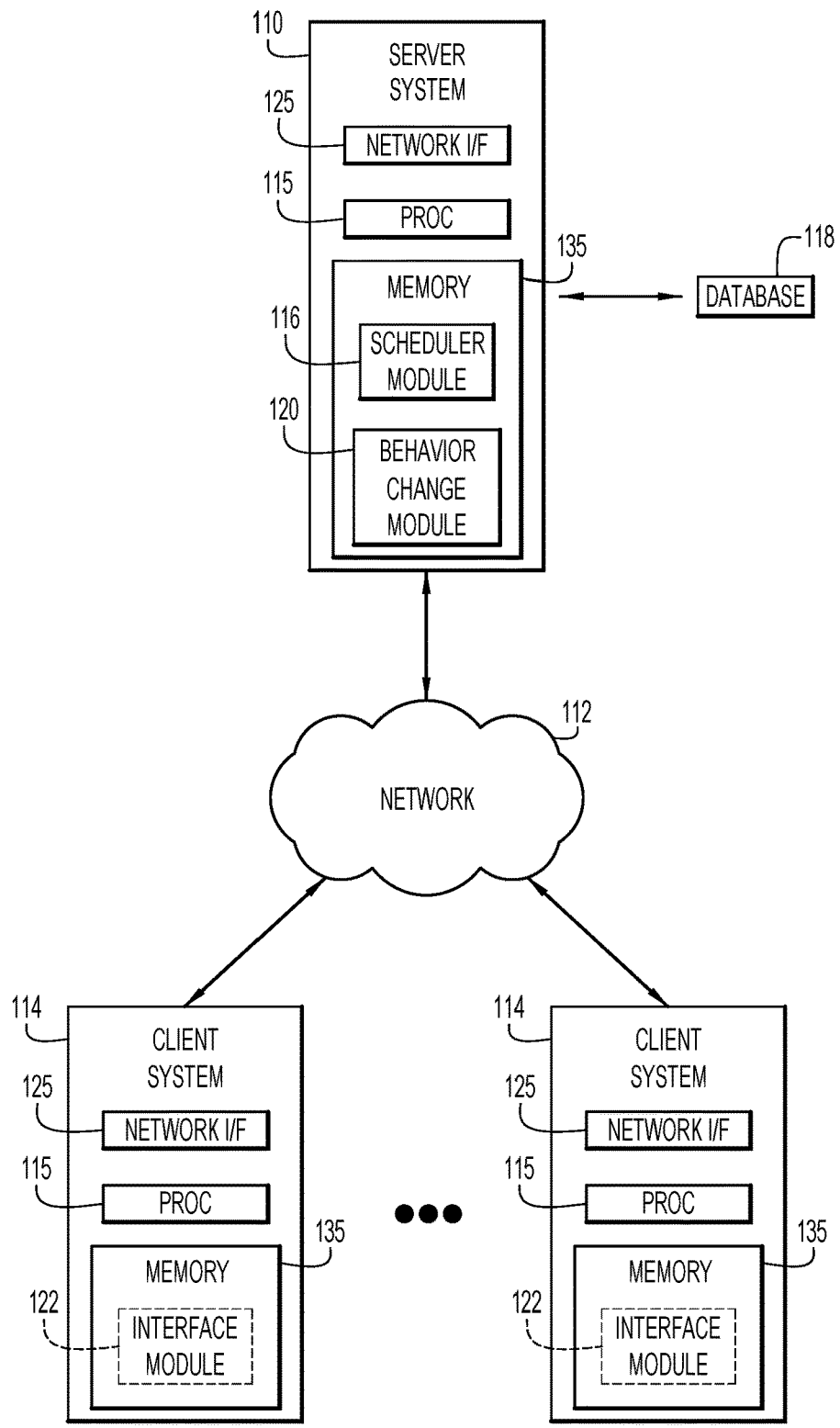
FIG. 1 is a diagrammatic illustration of an example computing environment of an embodiment of the present invention.

Present invention embodiments couple artificial intelligence and behavioral analytics to seize an individual's attention with an appropriate contextual intervention at the proper time for inducing a behavior change to achieve a desired health or life goal. An embodiment of the present invention monitors context and behavior of a user to generate a behavior history. One or more models are utilized to determine an intervention, personalized for that user, to induce a behavior modification, wherein the one or more models map interventions to a representation of the behavior change process and analyze the behavior history and context of an individual to determine an effective intervention for the user. The intervention is provided to the user and feedback is received in response to the intervention. The user's response to the intervention is used to update the models' belief about the user's state in the behavior change process. The one or more models are updated to learn a user behavior profile and interventions adjusting behavior of the user toward the behavior modification based on the models' belief about the user's state and/or context in the behavior change process.

An embodiment of the present invention, for a given targeted behavior change, dynamically updates a probabilistic mapping of a user to a multi-dimensional behavior change space by repeatedly selecting and providing the user with an intervention. The intervention may present one or more artifacts to the user, in different contexts, to measure the response of the user to the artifacts of the intervention and, ultimately induce the targeted behavior change. Interventions may provide a sequence of artifacts that eventually induce the desired change over time. The mapping is updated based on the current context, and the emotional and behavioral response of the user to the intervention. An intervention may include a set of one or more artifacts. An artifact may include: a notifications or message, a descriptive or predictive insight, a prescriptive recommendation, a question, a video, a telephone call, a coupon or other incentive, telephone/device settings, and/or other information to induce the targeted behavior change to achieve a desired health or life goal. Some attributes of the interventions may be dynamic or changeable. For example, an intervention message may indicate "By 2 PM today, you ate XX % of your daily carbohydrate limit", the "XX %" is dynamic (or dynamically determined) and reflects actual amount of consumed carbohydrates from the user's data.

The interventions are mapped to a behavior change space, and are selected to be provided to the user based on the current and historical mappings of the user to the behavior change space. The interventions may be created and/or selected to maximize the information gained about the user mapping, maximize the perceived usefulness of the intervention to the user, and/or influence a response of the user towards the targeted behavior to achieve a desired health or life goal. The response of the user may be measured over a time interval of finite duration.

Present invention embodiments employ a repository of data/knowledge of populations, cohorts, and individuals. Analysis of this data results in insights that are used to determine which individual is selected to induce behavior to achieve a desired health or life goal, when is the optimal time for an intervention for an individual, and how is the individual influenced for an optimal outcome. Outputs of present invention embodiments may be utilized to supplement the knowledge repository. A context-based repository is generated of interventions based on analytics. Interventions can be added, deleted, and/or modified by present invention embodiments. The interventions may be dynamically changed based on a context of the user, and the effectiveness of the intervention may be determined or updated from the immediate behavioral response to the intervention and from historical behaviors of the user. A feedback loop is employed for continuous learning and optimization of successful and unsuccessful interventions.

Present invention embodiments are behavior change framework agnostic, and various behavior change frameworks may be employed. Present invention embodiments learn to select an intervention and determine the time to best deliver the intervention to a user. Present invention embodiments characterize users and dynamically locate the users in the behavior change space to determine interventions.

An example environment for use with present invention embodiments is illustrated in FIG. 1. Specifically, the environment includes one or more server systems 110, and one or more client or end-user systems 114. Server systems 110 and client systems 114 may be remote from each other and communicate over a network 112. The network may be implemented by any number of any suitable communications media (e.g., wide area network (WAN), local area network (LAN), Internet, Intranet, etc.). Alternatively, server systems 110 and client systems 114 may be local to each other, and communicate via any appropriate local communication medium (e.g., local area network (LAN), hardwire, wireless link, Intranet, etc.).

Client systems 114 enable users to interact with server systems 110 to receive interventions and provide responses thereto. The server systems include a scheduler module 116 and a behavior change module 120. Scheduler module 116 schedules transmission of an intervention based on information from behavior change module 120. The behavior change module 120 determines an appropriate intervention to provide and the proper time and frequency of occurrence for the intervention. A database system 118 may store various information for the analysis (e.g., behavior profiles, population data, artifacts, intervention information, etc.). The database system 118 may be implemented by any conventional or other database or storage unit, may be local to or remote from server systems 110 and client systems 114, and may communicate via any appropriate communication medium (e.g., local area network (LAN), wide area network (WAN), Internet, hardwire, wireless link, Intranet, etc.).

The client systems 114 may present a graphical user (e.g., GUI, etc.) or other interface (e.g., command line prompts, menu screens, etc.) to provide and solicit information from users pertaining to an intervention, and may provide reports including analysis and behavior change results (e.g., progress towards attaining a goal, etc.). The client systems include an interface module 122 to provide the interface and interact with server systems 110. By way of example, the interface module 122 may include a browser for interacting with a network site hosted by server systems 110. Alternatively, the interface module 122 may include a local application that interacts with the server systems to receive interventions.

Server systems 110 and client systems 114 may be implemented by any conventional or other computer systems preferably equipped with a display or monitor, a base, optional input devices (e.g., a keyboard, mouse or other input device), and any commercially available and custom software (e.g., server/communications software, scheduler module, behavior change module, browser/interface software, etc.). The base preferably includes at least one hardware processor 115 (e.g., microprocessor, controller, central processing unit (CPU), etc.), one or more memories 135 and/or internal or external network interfaces or communications devices 125 (e.g., modem, network cards, etc.)). In addition, client systems 114 may be implemented by various portable computing devices (e.g., smartphone, tablet, laptop, etc.) to receive interventions.

Scheduler module 116, behavior change module 120, and interface module 122 may include one or more modules or units to perform the various functions of present invention embodiments described below. These modules may be implemented by any combination of any quantity of software and/or hardware modules or units, and may reside within memory 135 of the server and/or client systems for execution by processor 115.

Figure 2A:
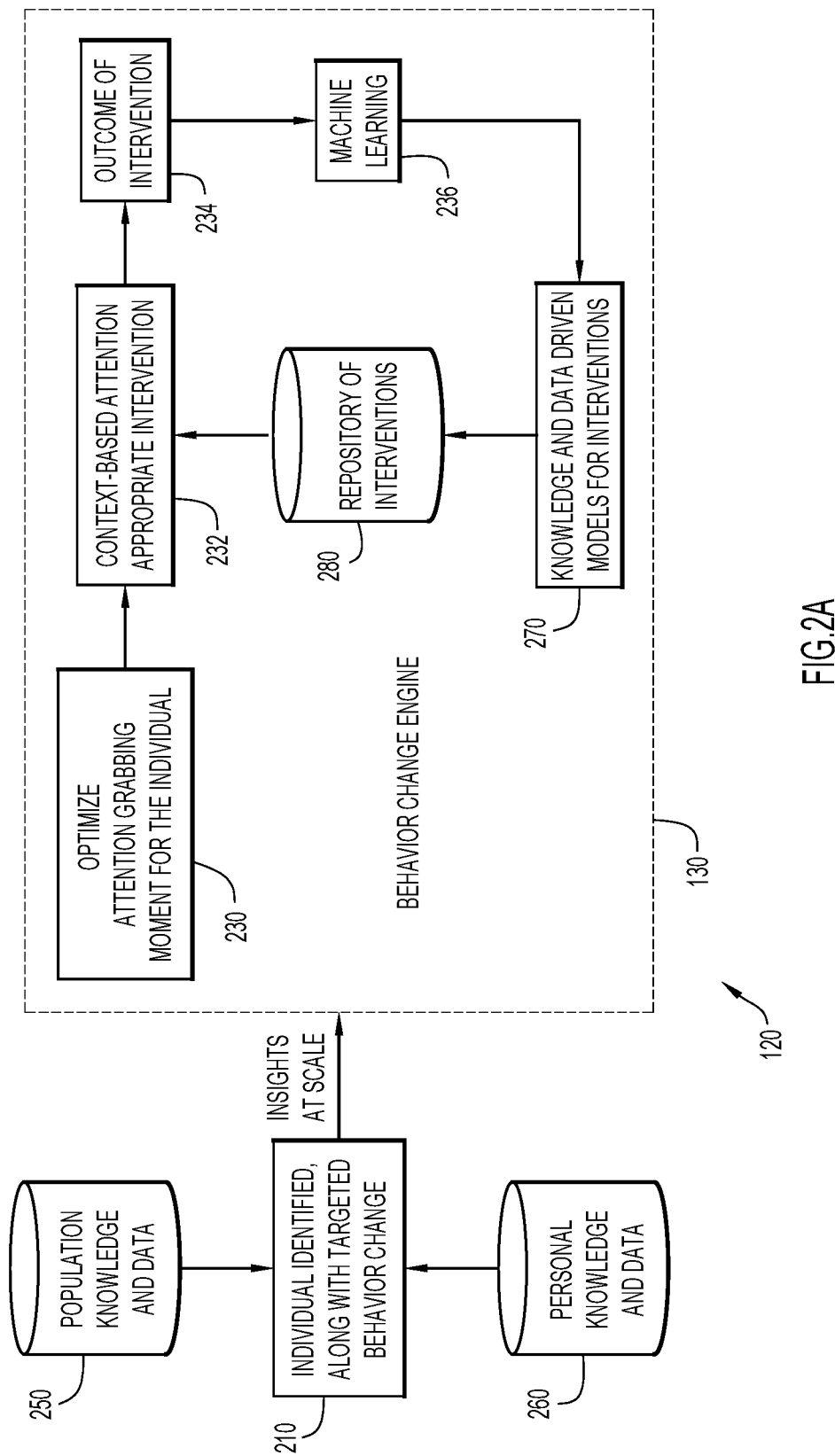
FIG. 2A is a flow diagram of a manner of generating personalized interventions for behavior modification based on machine learning according to an embodiment of the present invention.

A manner of establishing an intervention for a user (e.g., via scheduler module 116, behavior change module 120, and server system 110) according to an embodiment of the present invention is illustrated in FIG. 2A. Initially, population knowledge and personal knowledge are stored in repositories 250, 260, preferably residing within database system 118. This information is analyzed at flow 210 by scheduler module 116 to identify an individual along with a targeted behavior change to achieve a desired health or life goal. For example, the individual may be identified to change behavior to improve timely administration of medication. Insights from this determination are provided to a behavior change engine 130 of behavior change module 120. The behavior change engine optimizes an attention grabbing moment for the individual at flow 230 (e.g., determines a time for providing the individual with an intervention that most likely will induce the behavior change to achieve a desired health or life goal). This information is provided to determine a context-based intervention from a repository or library 280 at flow 232 (e.g., determines which intervention to utilize to optimally and dynamically select the individual for the behavior change intervention). Repository 280 preferably resides in database system 118. The interventions in repository 280 are mapped to behavior of the individual to induce the behavior change to achieve a desired health or life goal.

The outcome or effectiveness of the intervention is determined at flow 234 (e.g., effectiveness in changing behavior). For example, the effectiveness may be based on changes in timeliness of administration of medication of the individual. A feedback loop is utilized for continuous machine learning of the interventions that are successful for changing behavior to achieve a desired health or life goal at flow 236. This information is provided to learning models 270, which update selection of the interventions in repository 280. These learning models are described in more detail below and may be implemented using, for example, k-nearest neighbor, learned decision trees, matrix factorization, neural networks, and/or Bayesian classifiers techniques. In addition, the learning models may be implemented by a Watson system (developed by International Business Machines Corporation) that uses machine learning functionalities and algorithms to learn about the interventions and derive heuristic information governing the intervention selection.

Figure 2B:
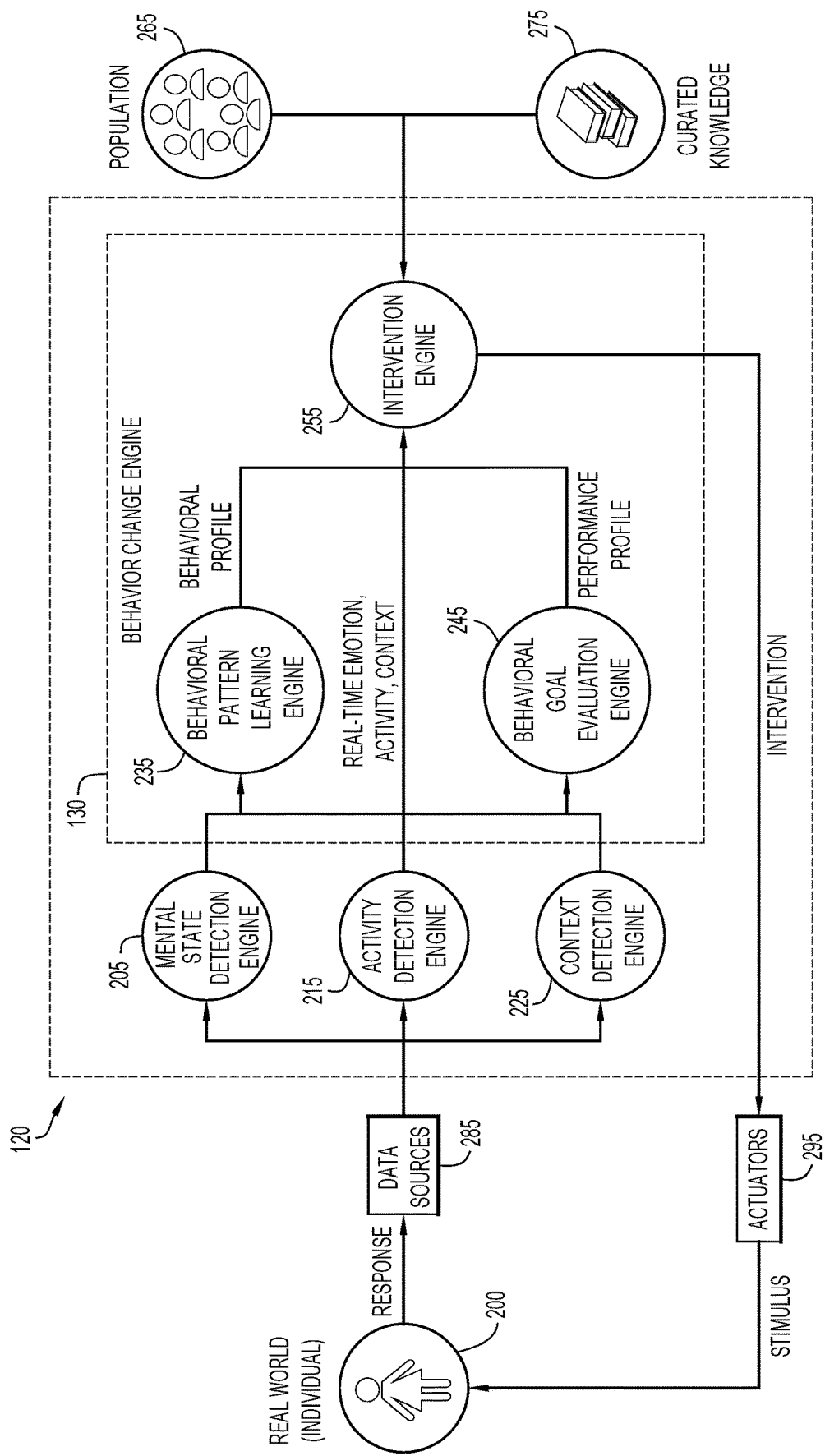
FIG. 2B is a flow diagram of a manner of generating personalized interventions in more detail according to an embodiment of the present invention.

Referring to FIG. 2B, an individual or user 200 may provide information to various data sources 285 (e.g., for monitoring of context and behavior, etc.). The provided information may reflect a response by the individual to some type of stimulus (e.g., derived from an intervention) to induce a behavior change. The data sources may include: wearable devices with one or more sensors to measure various physiological conditions of the individual (e.g., pulse or heart rate, activities, distance traveled, blood pressure, body temperature, speech slurring, a time a person is sitting or otherwise inactive, etc.); a portable computing device (e.g., smartphone, tablet, etc.) providing various information (e.g., preferences, personal information, personal or other contacts, schedule of events or appointments, communications with other individuals, speech and/or speech slurring, etc.) pertaining to the individual; image capture device or camera to capture images of the individual (e.g., facial expressions, etc.); social media or other network sites providing social or other information pertaining to the individual (e.g., personal preferences, social or other contacts, postings by the individual, etc.). The information from the data sources is provided to behavior change module 120 for processing.

Behavior change module 120 includes a mental state detection engine 205, an activity detection engine 215, a context detection engine 225, and behavior change engine 130. The mental state detection engine analyzes information from data sources 285 and determines emotions of the individual over time. The mental state detection engine 255 may use any technique to estimate or determine what emotion(s) the individual is currently experiencing. For example, some embodiments determine emotions of an individual based on a combination of heart rate variability (or pulse), movement analysis, and frequency of speech. Further, the individual's emotion may be ascertained and/or refined from textual information. For example, natural language processing (NLP) techniques may analyze textual information from the individual to determine the sentiment or mood of textual information of the individual, such as IBM's Watson Message Sentiment services. In addition, the emotion may be determined and/or refined based on image processing of images of facial expressions of the individual.

Activity detection engine 215 analyzes information from data sources 285 to determine activities (e.g., exercising, dining, working, watching entertainment, resting, etc.) performed by the individual over time. The activities may be derived from the physiological measurements (e.g., exercising, resting, etc.), geospatial measurements (e.g., accelerometers built into wearable devices, GPS sensors, etc.), and/or other information from data sources 285 (e.g., posting to social media sites of current activities, communications with others, etc.).

Context detection engine 225 analyzes information from data sources 285 and determines contexts of the individual over time. The context indicates a situation or state of the individual (e.g., time of day for the individual, an activity engaged in by the individual, characteristics of the individual (e.g., individual preferences, vital signs and other clinical characteristics, etc.), information pertaining to a calendar or schedule of the individual, etc.).

Engines 205, 215, 225 provide to behavior change engine 130 real-time information pertaining to the emotion, activity and context of the individual. The behavior change engine determines an intervention type, confidence scores or probabilities, timing (e.g., when to provide an intervention), and a frequency of occurrence for the intervention (e.g., how often to provide the intervention).

The behavior change engine 130 includes a behavioral pattern learning engine 235, a behavioral goal evaluation engine 245, and an intervention engine 255. The behavioral pattern learning engine 235 in this embodiment analyzes the emotion, activity, and context of the individual; generates an initial user behavior profile 350; and subsequently updates that user behavior profile as described below (FIG. 3B). User behavior profile 350 may be in the form of a table with rows representing behavior elements and columns representing intervention purposes. The behavior elements and intervention purposes may represent dimensions in the behavior change space. The user behavior profile basically learns how the user is feeling or functioning, and represents this in the user behavior profile based on responses by the individual to interventions.

The behavioral goal evaluation engine analyzes the emotion, activity, and context of the individual and updates a performance profile of the individual pertaining to a measurement of performance over time (e.g., maintaining activities to induce behavior modification to achieve a desired health or life goal, etc.). The performance profile may be compared to goals for the induced behavior modification to indicate a status of the individual with respect to those goals. For example, the behavioral goal evaluation engine may indicate trends of the individual with respect to the goals (e.g., progress, regress, sustained, etc.).

The intervention engine analyzes the emotion, activity and context of the individual, the behavior profile, and the performance profile to determine an appropriate and personalized intervention for the individual as described below. In addition, the intervention engine may utilize population information (or real world evidence) 265 and a knowledge base 275 to better determine the appropriate intervention. The population information and knowledge base preferably reside within database system 118. The population information may contain information pertaining to individuals of various populations defined by certain attributes (e.g., age, geographical location, goals, etc.). The knowledge base may contain known information pertaining to individual behavior and corresponding interventions (e.g., articles, literature, medical or other manuals, etc.).

The determined intervention is provided to the individual (e.g., as a stimulus) through an actuator or device 295 (e.g., computing device, wearable device, etc.) to induce the desired behavior change to achieve a desired health or life goal. For example, the individual may receive an intervention comprising one or more artifacts (e.g., on a wearable device, portable or other computing device, etc.), such as messages, insights, etc., to induce the desired behavior change to achieve a desired health or life goal. The individual may provide a response or feedback to the intervention (e.g., physical changes measured by a wearable device, user-provided feedback, etc.) to enable the behavior change engine to learn appropriate and successful interventions for the individual in order to attain the desired behavior modification to achieve a desired health or life goal.

Figure 3A:
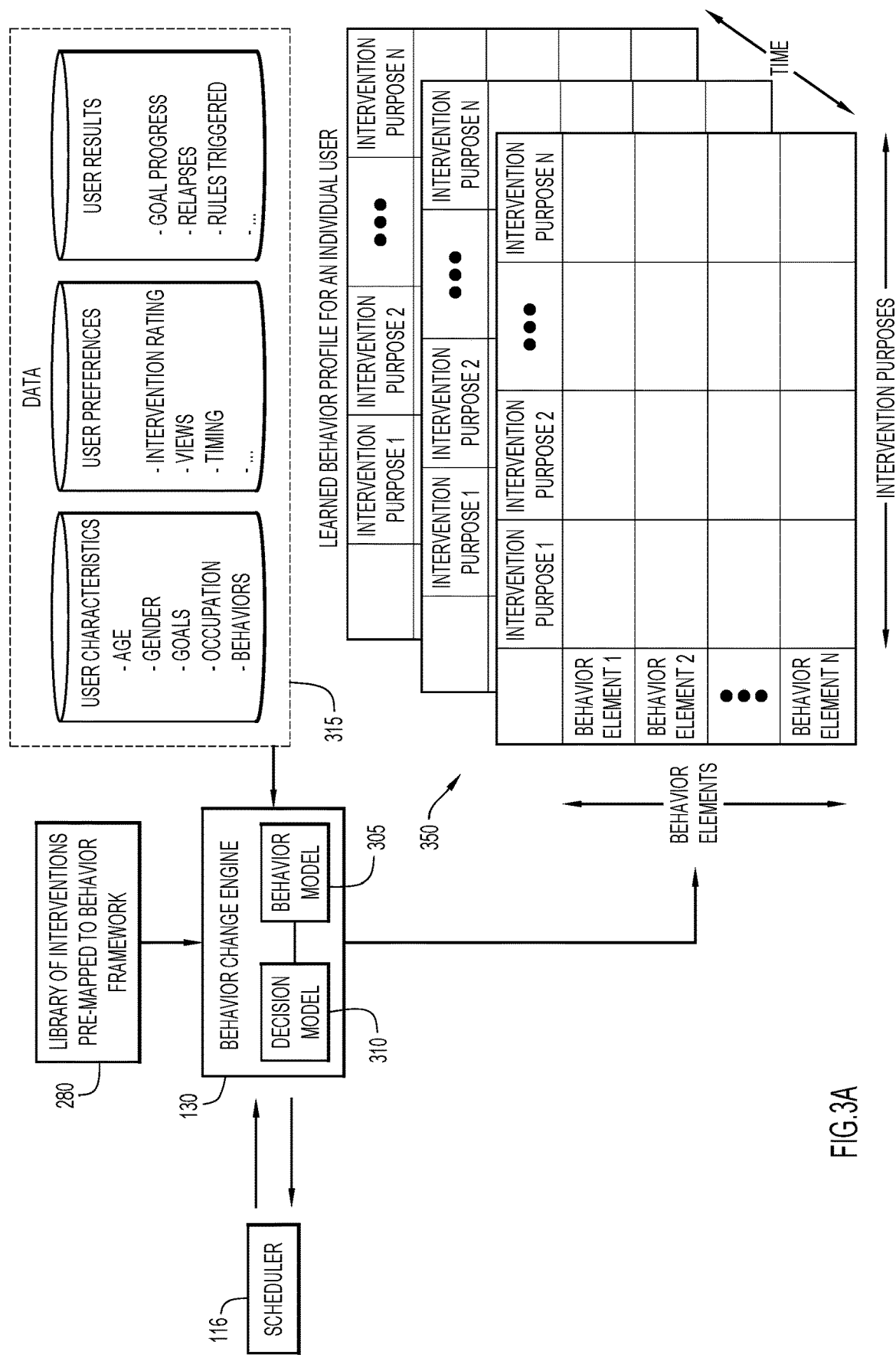
FIG. 3A is a diagrammatic illustration of an example architecture for generating personalized interventions for behavior modification according to an embodiment of the present invention.
Figure 3B:
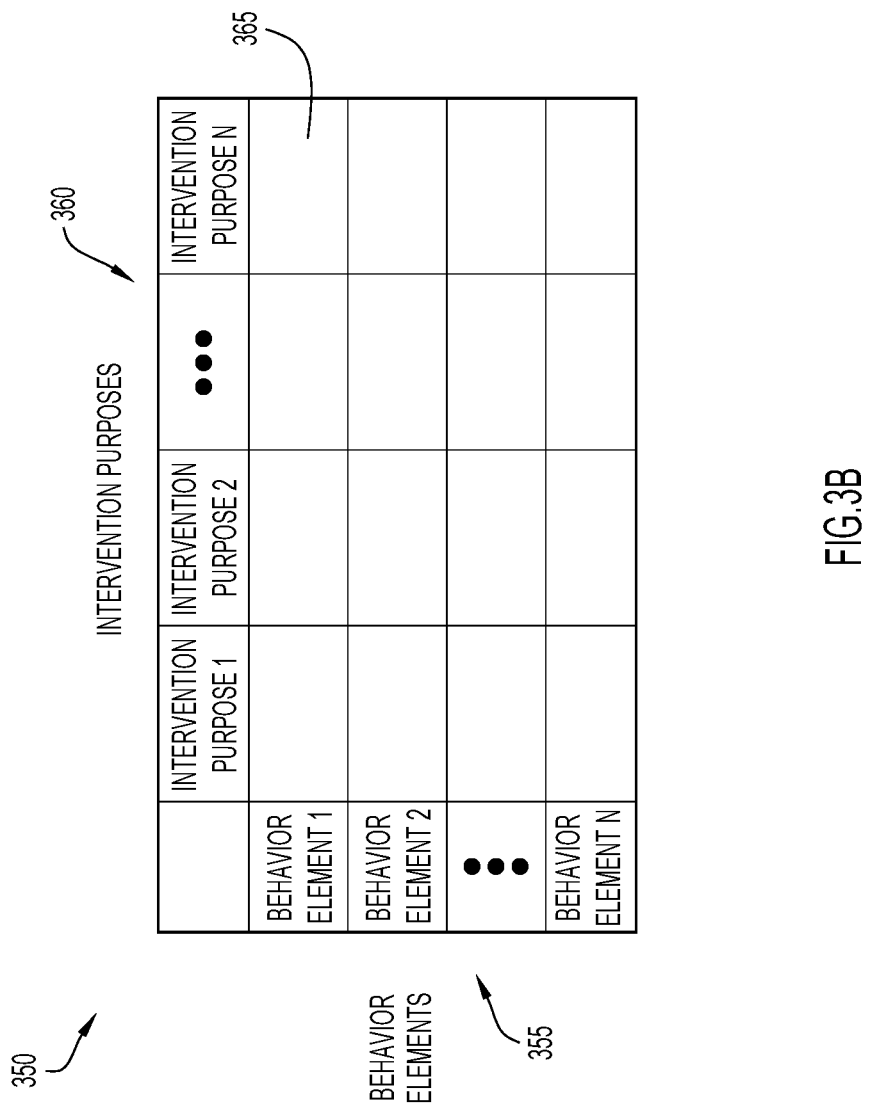
FIG. 3B is an example of a behavior profile of an individual according to an embodiment of the present invention.

Referring to FIGS. 3A and 3B, an embodiment of behavior change engine 130 includes behavioral pattern learning engine 235 with a behavior model 305, and intervention engine 255 with a decision model 310. The behavior change engine returns intervention purposes (mapped to interventions as described below) and confidence scores (or probabilities), timing (e.g., when to provide an intervention), and a frequency of occurrence for the intervention (e.g., how often to provide the intervention). The behavior change engine is coupled to various user data 315 (e.g., stored in database system 118) and repository or library 280 of interventions pre-mapped to a behavior change framework of user behavior profiles 350. By way of example, the user data may include user characteristics (e.g., age, gender, goals, occupation, behaviors, etc.), user preferences (e.g., intervention rating, views, timing, etc.), and user results (e.g., goal progress, relapses, rules triggered, etc.). The user results may be provided by behavioral goal evaluation engine 245. In addition, the interventions in repository 280 may each indicate an action, one or more artifacts, and/or one or more associated intervention purposes (from user behavior profile 350). The artifacts of an intervention may include notifications or messages, descriptive or predictive insights, prescriptive recommendations, questions, videos, telephone calls, coupons or other incentives, telephone/device settings, or other information to induce the targeted behavior change.

Behavior model 305 employs user behavior profiles 350 providing a behavior change space. A user behavior profile 350 (FIG. 3B) may be in the form of a table with rows 355 representing behavior elements and columns 360 representing intervention purposes. The behavior elements and intervention purposes may represent dimensions in the behavior change space. Each cell 365 (or intersection of an intervention purpose and behavior element) of user behavior profile 350 corresponds to a location in the behavior change space, and is mapped to an intervention in repository or library 280 corresponding to the intervention purpose associated with that cell.

Each cell 365 further indicates a probability that an intervention mapped to an associated intervention purpose produces the desired behavior change (or a positive response) with respect to the corresponding behavior element. Alternatively, each cell 365 may indicate a set of mathematical entities. For example, an element in the set may be a conditional probability distribution function that specifies a probability of changes in a behavior element, conditioned on the user adopting and adhering to the intervention at a rate of X %. Another element in the set may be a probability that the user adopts the intervention, while still another element in the set may be a probability distribution that specifies the probable adherence level to the intervention. The probability distributions may utilize any conventional or other probability distribution functions (e.g., Gaussian, Poisson, Bernoulli, etc.).

In addition, the user behavior profile may comprise probability distributions that consider plural cells simultaneously. For example, joint probability distributions may be defined across plural intervention purposes and behavior elements that describe the potential effectiveness of combinations of interventions on the targeted behavior change. Similarly, probability distributions may be defined that describe the potential effectiveness of a particular intervention to combinations of targeted behaviors. In some embodiments, the probability distributions utilize probability distribution functions (e.g., Gaussian, Poisson, Bernoulli, etc.).

The behavior elements of user behavior profile 350 may pertain to various behavioral aspects serving as a source of behavior (e.g., facilitators and barriers to behaviors, etc.), while the intervention purposes of user behavior model 350 may pertain to different aspects of the individual to stimulate to induce the desired behavior. The behavior elements and intervention purposes are each associated with features or attributes to identify a location of a user within the behavior change space. For example, user attributes may be compared to features of the behavior elements and intervention purposes to identify a cell of the user behavior profile (or location in the behavior change space) associated with the user. In some embodiments, the comparison utilizes similarity metrics (e.g. Euclidean distance, cosine similarity, matching, etc.).

By way of example, an embodiment of the present invention may employ a behavior change wheel framework. This framework utilizes behavior elements of capability-physical, capability-psychological, motivation-reflective, motivation-automatic, opportunity-physical, and opportunity-social, and intervention purposes of education, persuasion, incentivization, coercion, training, restriction, environmental restructuring, modeling, and enablement. However, user behavior profile 350 may also or alternatively be based on other behavior models or frameworks, and include any quantity of any desired behavior elements and intervention purposes.

Each user may be associated with a plurality of user behavior profiles each corresponding to a specified time and context, and behavior change target. The plurality of user behavior profiles over a time interval form a behavior history for the user that may be used to select an intervention. A user behavior profile may be initialized for a user based on behavior profiles of other similar users (e.g., using clustering, collaborative-based filtering, etc.). For example, similarity metrics (e.g. Euclidean distance, cosine similarity, etc.) may be determined to compare a target user against all other users (e.g., from population repository 265) based on demographic data (e.g. age, gender, occupation, education level, medical conditions, etc.). Users that score highly in the similarity metric may be grouped into a similarity cohort. The responses to interventions (and/or corresponding probabilities) from other users in the cohort may be used to establish an initial behavior profile (in lieu of responses from the target user).

Features are generated from raw data pertaining to the user, such as user data 315. By way of example, the features may include average or standard deviation for user ratings or feedback for interventions, intervention view duration, click or input rates, increase in progress for a goal, number of relapses, number of rules triggered, etc. The rules define an event (e.g., the user has exceeded their daily recommended maximum of calories from fats, a risk of exceeding the daily total caloric intake within the next hour has exceeded 75%, etc.). A list of events is defined, where the rules are a quantifiable and measurable specification of the events in order to detect occurrence of the event. The triggering of the rules indicates occurrence of the associated events, and may be detected by behavior change engine 130 and used by behavioral goal evaluation engine 245 to update a user performance profile.

Behavior model 305 learns user preferences (e.g., via content-based recommendations, reinforcement learning, etc.), and computes an explicit preference score for each intervention purpose (and intervention) provided for a corresponding context at a corresponding time. This score indicates a user's shared feedback on the mapped intervention (of the intervention purpose) provided for the context at a certain time period, and is based on user feedback or ratings (e.g., thumbs up or thumbs down, star rating, etc.) with respect to a specific intervention. User response for the explicit preference score may be measured based on any suitable feedback from the user with respect to an intervention, such as ratings and questionnaires (e.g., inquiring about the types of insights liked, the behaviors interested in being changed, the manner of being notified, etc.).

By way of example, an explicit preference score may be determined by adding positive preferences (e.g., thumbs up, high star rating, etc.) and subtracting negative preferences (e.g., thumbs down, low star rating, etc.) toward an intervention purpose. The positive and negative preferences may be combined in a weighted manner (e.g., assigning any desired weights to the preferences). In addition, learning models may be employed to determine the explicit preference score (e.g., k-nearest neighbor, learned decision trees, matrix factorization, neural networks, etc.). The learning models may receive inputs, such as the positive and negative preferences, etc., and be trained to provide an explicit preference score as output based on an initial training set. The learning models may dynamically be updated based on new preference inputs.

An implicit preference score is also calculated for each intervention purpose provided for a corresponding context at a corresponding time. This score indicates behavior goal or sub-goal progress (e.g., what the user does) after the mapped intervention (of the intervention purpose) is provided for a context at a corresponding time, and is based on passive data/features of the user, such as those described above (e.g. goal progress, timestamp from when the intervention was viewed, intervention view duration, reduction in relapses, reduction in rules triggered, etc.). The goal progress may be based on the performance profile provided by behavioral goal evaluation engine 245.

By way of example, an implicit preference score may be determined by adding occurrences of positive indicators (e.g., goal progress, sufficient viewing duration, fast response to intervention, etc.) and subtracting occurrences of negative indicators (e.g., goal regression, minimal viewing duration, non-responsive to interventions, etc.) toward an intervention purpose. The positive and negative indicators may be combined in a weighted manner (e.g., assigning any desired weights to the indicators, etc.). In addition, learning models may be employed to determine the implicit preference score (e.g., k-nearest neighbor, learned decision trees, matrix factorization, neural networks, etc.). The learning models may receive inputs, such as the positive and negative indicators, etc., and be trained to provide an implicit preference score as output based on an initial training set. The learning models may dynamically be updated based on new indicator inputs.

The explicit and implicit preference scores and features are used to compute an updated probabilistic belief (or probability) for a user behavior profile for the corresponding time period and context. The cells of the user behavior profile may contain the probability (or set of mathematical entities), and/or utilize various schemes to represent those probabilities or entities (e.g., color-coding of cells, etc.).

Whenever a new explicit or implicit preference score is calculated, the corresponding cells (probabilities or mathematical entities) are updated. The cells are continuous and color coding may be utilized according to a specific use case of the behavior change engine. For example, a red-to-green scheme may indicate a low to high probability of a positive response to an associated intervention. The probabilities (or mathematical entities) are computed using intervention attributes or features (e.g., of the cell) that characterize the intervention in the behavior change space, and positive and negative user responses to the intervention. As described above, examples of user responses to an intervention may include a thumbs up or thumbs down rating presented as a notification, or detecting that the user has (or has not) engaged in the targeted behavior change some time after receiving the intervention. These responses may be used to create a probability distribution of user preferences over the behavior change space. The probability distribution may utilize any conventional or other probability distribution functions (e.g., Gaussian, Poisson, Bernoulli, etc.).

By way of example, the probability distribution may be determined by averaging and normalizing the positive and negative user responses over the intervention behavior change space features. Alternatively, machine learning may be employed to predict the probability that a user will have a positive response to interventions with a behavior change space feature. The machine learning may employ any learning models (e.g. neural networks, Bayesian classifiers, deep learning, matrix factorization, k-nearest neighbor, etc.). The learning models may receive inputs, such as the explicit and implicit preference scores, etc., and be trained to provide an indication of a positive or negative user response to an intervention based on an initial training set. In other words, the user behavior profile is learned by the learning models. Further, the user context, emotion, and/or other information (e.g., from population information 265 and/or knowledge base 275) may be inputs for the learning models. For example, learning may occur from the target user, and/or other users that are similar to the target user. Data from other users (e.g., population information 265) may be used by the learning models to help determine which interventions a target user may respond positively. The target user data may be supplemented with data from other users in situations where data from the target user is sparse, or limited to a subset of dimensions of the behavior change space.

The learning models produce a probability during processing in order to determine the resulting indication (e.g., a determined probability may be compared to a threshold or otherwise processed by the model to produce the resulting indication). The probability from the learning models may be used to update the cell of the corresponding user behavior profile. The learning models may dynamically be updated based on new inputs.

Decision model 310 determines the intervention purpose, timing, and frequency of occurrence of an intervention depending on the belief or probability on the user behavior profile (where the intervention purposes associated with the cells of the user behavior profile are mapped to the interventions in repository or library 280). The decision model determines a location of the user in the behavior change space based on the user context and attributes. For example, the user context may be used to identify the corresponding user behavior profile of an associated time, while the user attributes may be compared to the attributes of the behavior elements of that user behavior profile to identify a corresponding behavior element. The intervention purposes for the identified behavior element are analyzed by the decision model to determine a resulting intervention purpose (that is mapped to a corresponding intervention). This may be based on comparisons of attributes of the user and the intervention purposes, and/or the probabilities in the user behavior profile (e.g., indicating the intervention purpose for the identified behavior element most likely to produce a positive response). In addition, the user context may be employed as a constraint, and/or other information (e.g., from population information 265 and/or knowledge base 275) may be used, to determine the resulting intervention purpose (or intervention).

The timing and frequency of an intervention is determined for a specific use case based on a specified set of timing and frequency, where an optimum timing and frequency for an intervention is learned from explicit and implicit preference scores. For example, an initial set of timing and frequency may be modified based on rules or other criteria (e.g., adjust the timing and frequency by fixed or variable time and frequency adjustments, such as one or more minutes and one or more occurrences pursuant to a corresponding condition or rule (e.g., designating explicit and/or implicit preference scores), etc.). Alternatively, machine learning may be employed to determine the timing and frequency for an intervention. The machine learning may employ any quantity of any learning models (e.g. neural networks, Bayesian classifiers, deep learning, matrix factorization, k-nearest neighbor, etc.). The learning models may receive inputs, such as the intervention purpose, prior sets of timing and frequency for the intervention purpose, explicit and implicit preference scores, etc., and be trained to provide an indication of a timing and frequency for the intervention purpose based on an initial training set. In addition, the user context and/or other information (e.g., from population information 265 and/or knowledge base 275) may also be utilized as an input for the learning models.

The decision model may employ any rule-based approaches, model-based approaches (e.g. trees, dynamic programming, q-learning, etc.), and/or deterministic or stochastic (e.g., exploration vs. exploitation tradeoffs) approaches to analyze the information and determine the intervention purpose, timing, and frequency of occurrence.

The behavior and decision models may initially be simplistic, and subsequently become more complex or evolve (e.g., based on learning, feedback, etc.) over time. These models may be implemented by a Watson system (developed by International Business Machines Corporation) that uses machine learning functionalities and algorithms to learn about the interventions and derive heuristic information governing the intervention selection. The interventions provide insights that address the full range of behavior elements, and are sent to users in an intelligent way based on personalized metrics.

Scheduler module 116 provides a request to behavior change engine 130 to determine the intervention purpose to provide the mapped intervention to a client system 114. The behavior change engine processes the request and provides one or more intervention purposes and corresponding confidence or probability scores (from user behavior profile 350), timing for providing interventions, and frequency of occurrence for interventions. The scheduler module retrieves the mapped interventions from repository 280 based on the intervention purposes, and provides the mapped interventions to the user at the specified time and frequency of occurrence.

Figure 4:
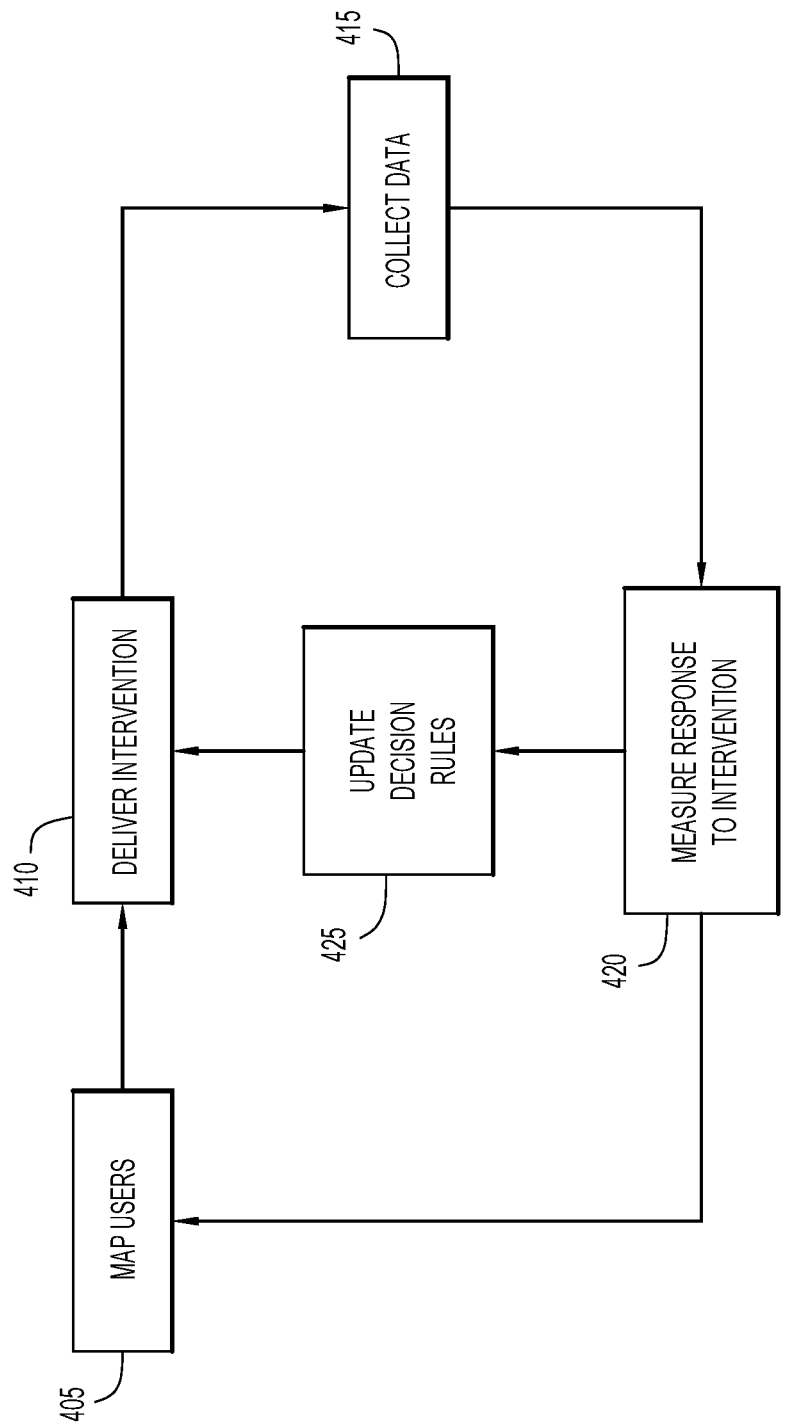
FIG. 4 is flow diagram of a manner of providing and dynamically modifying interventions for behavior modification according to an embodiment of the present invention.

A manner of providing and dynamically altering interventions for a user to induce a desired behavior modification to achieve a desired health or life goal (e.g., via scheduler module 116, behavior change module 120 and a server system 110) according to an embodiment of the present invention is illustrated in FIG. 4. Initially, a target behavior modification for a user is identified, and user behavior profiles are generated as described above. For example, the target behavior modification may be for the user to achieve a desired health or life goal, such as improve timeliness of administering medication. A user location within the behavior change space is initialized by the behavior change engine and may be based on user context, user attributes, behavior element attributes, and/or corresponding probabilities/confidences (e.g., similarities to other users, etc.) at flow 405. This may be based on the initial user behavior profile, and quantifies the barriers to the user behavior change. The location in the behavior change space is utilized by the behavior change engine to identify an associated intervention purpose (since the location is defined by the behavior change space dimensions of the behavior elements and intervention purposes). The intervention mapped to the associated intervention purpose is provided by the scheduler module to the user at flow 410. The artifacts of the mapped intervention are presented to and engaged by the user to induce the desired behavior change. For example, the intervention may include artifacts comprising notifications to administer the medication, positive results of taking the medication, etc.

The user response to the intervention is collected by the behavior change engine at flow 415, and measured at flow 420. This may be accomplished by converting raw data into response metrics or features of interest, such as those described above. The user behavior profile and decision model are updated based on the response metrics at flow 425. For example, the decision model may employ a rules-based approach, where the rules for selecting an intervention purpose may be dynamically modified based on the user response to the intervention. Further, the probabilities in the user behavior profile may be modified based on updated explicit and implicit preference scores and features as described above.

Resulting changes in user behavior from the intervention may alter the location of the user in the behavior change space. For example, the updated probabilities in the user behavior profile history and/or updated rules may alter the location of the user in the behavior change space. Accordingly, the user location is updated in the behavior change space, and the above process may be repeated to identify further interventions based on the updated location of the user in the behavior change space.

Present invention embodiments may be utilized for providing any types of interventions for inducing various changes to any types of behaviors (e.g., taking medications, exercising, eating habits, work habits, attain goals, etc.). For example, the interventions may include health and wellness interventions (e.g., medication adherence interventions to ensure one takes their medication, interventions for an annual or periodic physical examination, interventions for an annual or periodic mammogram, interventions for smoking cessation, interventions for opioid/alcohol use, etc.) and lifestyle interventions (e.g., interventions for diet, interventions for exercise, interventions for stress management, interventions for sleep management, etc.).

It will be appreciated that the embodiments described above and illustrated in the drawings represent only a few of the many ways of implementing embodiments for providing personalized intervention based on machine learning of behavior change states.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, scheduler module, behavior change module, interface module, etc.). These systems may include any types of monitors and input devices (e.g., keyboard, mouse, voice recognition, etc.) to enter and/or view information.

It is to be understood that the software (e.g., scheduler module, behavior change module, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

Embodiments of the present invention may also be delivered as part of a service engagement with an individual, hospital, a client corporation, nonprofit organization, government entity, internal organizational structure, or the like. These embodiments may include configuring a computer system to perform, and deploying software, hardware, and web services that implement, some or all of the methods described herein.

The software of the present invention embodiments (e.g., scheduler module, behavior change module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., behavior profiles, population data, artifacts, etc.). The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information (e.g., interventions, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include any information arranged in any fashion, and may be configurable based on rules or other criteria to provide desired information to a user (e.g., interventions, etc.).

The present invention embodiments are not limited to the specific tasks or algorithms described above, but may be utilized for providing interventions for inducing various changes to any types of behaviors (e.g., taking medications, exercising, eating habits, work habits, attain goals, etc.). The embodiments of the present invention may employ any behavior change framework or model having any quantity of any types of behavior elements and interventions (or intervention types or purposes). The interventions may include any quantity of any types of artifacts or items, and be sent at any desired times and frequencies of occurrence for any desired time durations (e.g., hours, days, weeks, months, years, etc.). The interventions may be provided in any quantity or combination (e.g., any quantity or combination of interventions of different types may be provided, etc.).

The user behavior profile may be implemented in any suitable data structure, and include any indications of a likelihood of a positive or negative response (e.g., probability, counts, etc.). The user feedback may include any type of information providing preferences of a user to an intervention or any components thereof (e.g., specific items or artifacts, etc.). The embodiments of the present invention may employ any quantity of any types of learning, rule-based, mathematical, or other models to learn user behavior and dynamically adjust selection and transmission of interventions for positive responses.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of providing an intervention for a user comprising:

monitoring behavior and context of a user, via a processor, to generate a behavior history, wherein the behavior history includes one or more user behavior profiles each with a plurality of dimensions including elements of behavior and purposes of interventions that define a behavior change space;

determining, via a plurality of models of a processor, an intervention for the user to induce a behavior modification, wherein the plurality of models map interventions to user context and behavior and utilize the behavior history to determine an effective intervention for the user based on a location of the user within the behavior change space determined in accordance with a probability of a positive response to the intervention and user attributes in relation to attributes of the plurality of dimensions, wherein one or more first machine learning models of the plurality of models determine a time and frequency of occurrence for sending the intervention based on the probability of a positive response to the intervention, wherein one or more second machine learning models of the plurality of models determine the probability of a positive response for one or more corresponding locations within the behavior change space from preference scores for responses to the intervention and progress of goals, wherein the preference scores include an explicit preference score determined by adding instances of positive feedback and subtracting instances of negative feedback of the user toward an intervention purpose, and an implicit preference score determined by adding occurrences of positive indicators for goal progress and subtracting occurrences of negative indicators for goal progress of the user toward the intervention purpose, and wherein determining an intervention comprises:

training the one or more second machine learning models with the preference scores pertaining to the user to determine the probability of a positive response for the user; and training the one or more second machine learning models with additional preference scores of other users in a population to supplement learning by the one or more second machine learning models for determining the probability of a positive response for the user;

sending the intervention to the user, via a processor, at the determined time and frequency of occurrence and receiving feedback in response to the intervention;

updating the plurality of models, via a processor, based on the feedback, wherein the probability of a positive response from the updated plurality of models enables the location of the user to change within the behavior change space; and sending, via a processor, the intervention at a time and frequency of occurrence determined by the updated plurality of models in accordance with the changed location of the user in the behavior change space.

2. The method of claim 1, wherein the determined intervention includes information relevant to inducing the behavior modification, and comprises one of a health and wellness intervention and a lifestyle intervention.

3. The method of claim 1, wherein the one or more user behavior profiles are associated with a corresponding behavior target and user context.

4. The method of claim 3, wherein a plurality of interventions are stored in a repository, and the determined intervention is selected from among the plurality of stored interventions.

5. The method of claim 4, wherein the purposes of interventions are mapped to corresponding ones of the plurality of stored interventions.

6. The method of claim 1, wherein the plurality of models use aggregated evidence from population data to determine the intervention.

7. A system for providing an intervention for a user comprising:

at least one processor configured to:

monitor behavior and context of a user to generate a behavior history, wherein the behavior history includes one or more user behavior profiles each with a plurality of dimensions including elements of behavior and purposes of interventions that define a behavior change space;

determine an intervention for the user to induce a behavior modification via a plurality of models, wherein the plurality of models map interventions to user context and behavior and utilize the behavior history to determine an effective intervention for the user based on a location of the user within the behavior change space determined in accordance with a probability of a positive response to the intervention and user attributes in relation to attributes of the plurality of dimensions, wherein one or more first machine learning models of the plurality of models determine a time and frequency of occurrence for sending the intervention based on the probability of a positive response to the intervention, wherein one or more second machine learning models of the plurality of models determine the probability of a positive response for one or more corresponding locations within the behavior change space from preference scores for responses to the intervention and progress of goals, wherein the preference scores include an explicit preference score determined by adding instances of positive feedback and subtracting instances of negative feedback of the user toward an intervention purpose, and an implicit preference score determined by adding occurrences of positive indicators for goal progress and subtracting occurrences of negative indicators for goal progress of the user toward the intervention purpose, and wherein determining an intervention comprises:

training the one or more second machine learning models with the preference scores pertaining to the user to determine the probability of a positive response for the user; and training the one or more second machine learning models with additional preference scores of other users in a population to supplement learning by the one or more second machine learning models for determining the probability of a positive response for the user;

send the intervention to the user at the determined time and frequency of occurrence and receive feedback in response to the intervention;

update the plurality of models based on the feedback, wherein the probability of a positive response from the updated plurality of models enables the location of the user to change within the behavior change space; and send the intervention at a time and frequency of occurrence determined by the updated plurality of models in accordance with the changed location of the user in the behavior change space.

8. The system of claim 7, wherein the determined intervention includes information relevant to inducing the behavior modification, and comprises one of a health and wellness intervention and a lifestyle intervention.

9. The system of claim 7, wherein the one or more user behavior profiles are associated with a corresponding behavior target and user context.

10. The system of claim 9, wherein a plurality of interventions are stored in a repository, and the determined intervention is selected from among the plurality of stored interventions.

11. The system of claim 10, wherein the purposes of interventions are mapped to corresponding ones of the plurality of stored interventions.

12. A computer program product for providing an intervention for a user, the computer program product comprising one or more computer readable storage media collectively having program instructions embodied therewith, the program instructions executable by at least one processor to cause the at least one processor to:

monitor behavior and context of a user to generate a behavior history, wherein the behavior history includes one or more user behavior profiles each with a plurality of dimensions including elements of behavior and purposes of interventions that define a behavior change space;

determine an intervention for the user to induce a behavior modification via a plurality of models, wherein the plurality of models map interventions to user context and behavior and utilize the behavior history to determine an effective intervention for the user based on a location of the user within the behavior change space determined in accordance with a probability of a positive response to the intervention and user attributes in relation to attributes of the plurality of dimensions, wherein one or more first machine learning models of the plurality of models determine a time and frequency of occurrence for sending the intervention based on the probability of a positive response to the intervention, wherein one or more second machine learning models of the plurality of models determine the probability of a positive response for one or more corresponding locations within the behavior change space from preference scores for responses to the intervention and progress of goals, wherein the preference scores include an explicit preference score determined by adding instances of positive feedback and subtracting instances of negative feedback of the user toward an intervention purpose, and an implicit preference score determined by adding occurrences of positive indicators for goal progress and subtracting occurrences of negative indicators for goal progress of the user toward the intervention purpose, and wherein determining an intervention comprises:

training the one or more second machine learning models with the preference scores pertaining to the user to determine the probability of a positive response for the user; and training the one or more second machine learning models with additional preference scores of other users in a population to supplement learning by the one or more second machine learning models for determining the probability of a positive response for the user;

send the intervention to the user at the determined time and frequency of occurrence and receive feedback in response to the intervention;

update the plurality of models based on the feedback, wherein the probability of a positive response from the updated plurality of models enables the location of the user to change within the behavior change space; and send the intervention at a time and frequency of occurrence determined by the updated plurality of models in accordance with the changed location of the user in the behavior change space.

13. The computer program product of claim 12, wherein the determined intervention includes information relevant to inducing the behavior modification, and comprises one of a health and wellness intervention and a lifestyle intervention.

14. The computer program product of claim 12, wherein the one or more user behavior profiles are associated with a corresponding behavior target and user context.

15. The computer program product of claim 14, wherein a plurality of interventions are stored in a repository, and the determined intervention is selected from among the plurality of stored interventions.

16. The computer program product of claim 15, wherein the purposes of interventions are mapped to corresponding ones of the plurality of stored interventions.

17. The computer program product of claim 12, wherein the plurality of models use aggregated evidence from population data to determine the intervention.

* * * * *